United States Patent [19]

Bell, III et al.

[11] 4,039,569

[45] Aug. 2, 1977

[54] METHYL CHLOROFORMATE PROCESS

[75] Inventors: Fred S. Bell, III, Baltimore, Md.; Ronald D. Crozier, Bedford, N.Y.; Lawrence Evans Strow, Baltimore, Md.

[73] Assignee: Minerec Corporation, New York, N.Y.

[21] Appl. No.: 685,436

[22] Filed: May 11, 1976

[51] Int. Cl.² ............................................. C07C 68/02
[52] U.S. Cl. .................................................... 260/463
[58] Field of Search ........................................ 260/463

[56] References Cited

U.S. PATENT DOCUMENTS

| 2,476,637 | 7/1949 | Strain et al. | 260/463 |
| 3,560,547 | 2/1971 | Hill | 260/463 |
| 3,910,983 | 10/1975 | Merkel et al. | 260/463 |

Primary Examiner—Delbert R. Phillips
Attorney, Agent, or Firm—James J. Burke

[57] ABSTRACT

A continuous process for producing high-purity methyl chloroformate, by reacting liquid methanol with an excess of phosgene at no more than 20° C., preferably about 15° C. Phosgene is absorbed in a large circulating load of pre-formed chloroformate that has also methanol added to it. The product stream is treated to remove light ends, and a 98% pure product results.

15 Claims, 1 Drawing Figure

U.S. Patent  Aug. 2, 1977  4,039,569
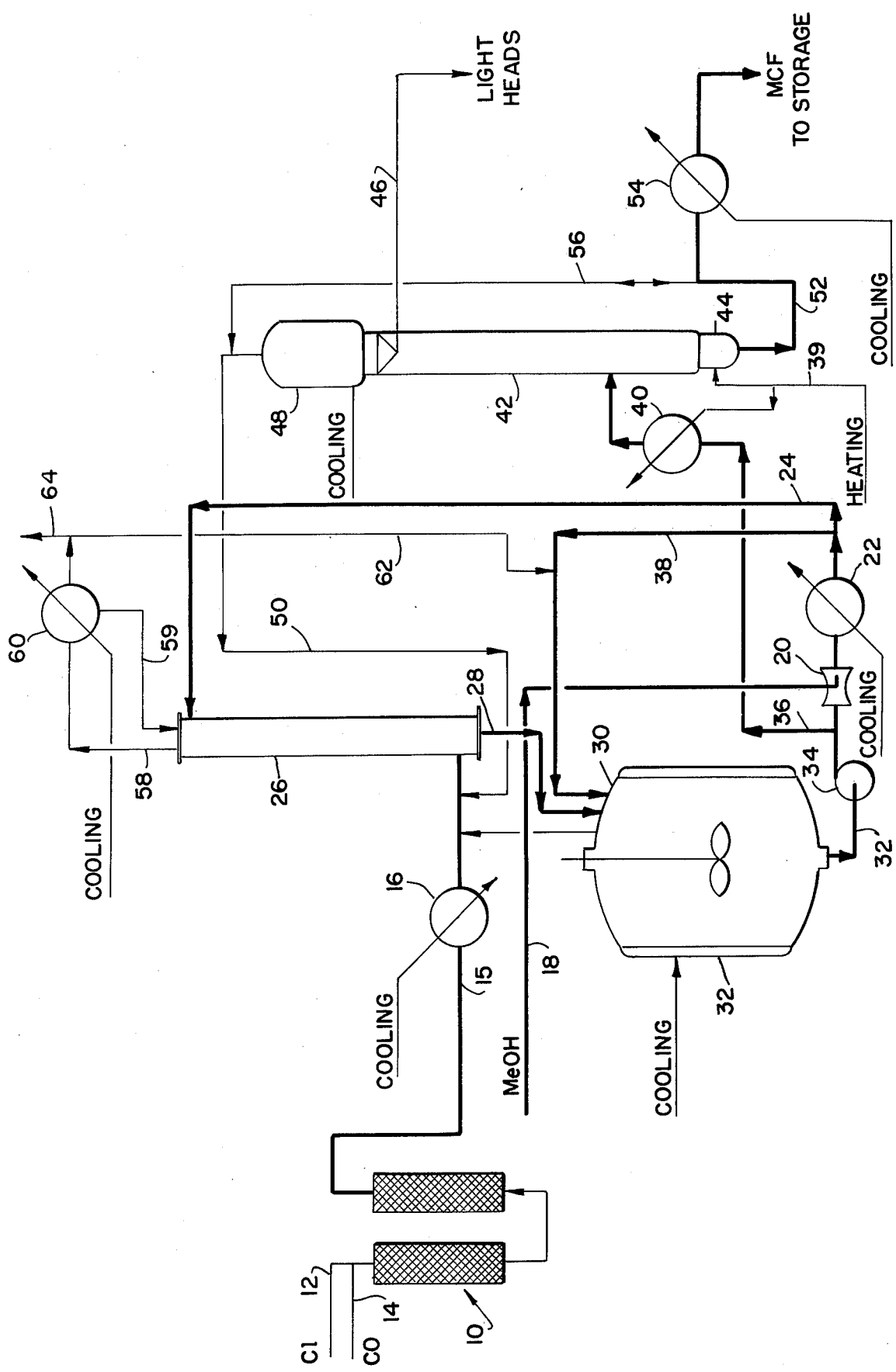

METHYL CHLOROFORMATE PROCESS

BACKGROUND OF THE INVENTION

The present invention relates to the preparation of methyl chloroformate, a composition of known utility as an intermediate in the manufacture of pharmaceuticals, agrichemicals, plastics and other organic compositions.

Methyl chloroformate has a molecular weight of 94.50 and a boiling point of 71.4° C. Its structure is characterized roughly as follows:

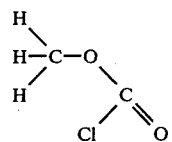

This structure is believed to account for the relative stability of the composition.

Methyl chloroformate ("MCF") is formed by the reaction of methanol with phosgene. Heretofore, this has been carried out in the gaseous phase in a countercurrent reactor packed with ceramic or activated carbon. Purities achieved by this method have not been good: about 85% is as good as can be expected. The major contaminants are dimethyl carbonate ("DMC"), methyl chloride, water, HCl, and phosgene (BP=8.02° C.) Heretofore, production of a high purity product has required distillation of this crude product.

Methyl alcohol, even if in excess of phosgene, can be "flashed" or distilled off and therefore is not a serious problem per se. However, excess methyl alcohol reacts with MCF, and the result is DMC. For this reason, the reaction should be run with an excess of phosgene. A second way DMC can be formed is by running the MCF reaction too hot. DMC can also be formed by reaction of excess methyl alcohol with MCF in the still, while the methyl alcohol is being flashed off. Since the DMC reaction is slow, this leaves little to worry about unless the still is left on total reflux for a long period of time. For every 1 wt.-% of methyl alcohol that reacts with MCF in a closed system, 2.95 wt.-% loss in the purity of MCF occurs, 2.81 wt.% gain in DMC occurs, and 1.14 wt.-% gain in HCl occurs.

If the MCF is above 53° C. HCl gas will be evolved because of limited solubility. In that case, the temperature would have to be lower for HCl gas not to evolve. For example: if a MCF solution containing 99% MCF and 1% methyl alcohol totally reacts due to time, temperature, or a combination, the ultimate result would be 96.05% MCF, 2.81% DMC, and 1.14% HCl or about 3% MCF purity loss.

Hydrogen chloride is another of the lesser contaminants of MCF. It is soluble in the range of 0.10 wt.-% at 71° C. to 3.25 wt.-% at 15° C. in MCF. As a by-product of the MCF preparation, HCl is almost impossible to completely eliminate and is at this time believed to be responsible for two problems. The first is the loss of MCF as a vapor along with the exiting HCl gas. This vaporizing effect due to the low vapor pressure of HCl lowers the MCF yield by as much as 20%, if sufficient cooling is not applied to the gas stream. This yield is based on the lowest concentration of raw material used, which is methyl alcohol. The second problem is the reaction of HCl gas with unreacted methyl alcohol in the MCF production. This is a catalytic effect accelerated by use of ceramic (clay) packing in the reaction column. The end products of this unwanted side reaction are methyl chloride and water. Methyl chloride is a gas at 15° C., evolves mixed with HCl gas.

Water is insoluble in MCF and vice versa. It is somewhat difficult to separate from MCF, but rapid distillation (flash-off) with some total reflux followed by total take-off will usually rid the MCF of most of the water and a good part of the excess methyl alcohol. MCF is decomposed by water and under certain conditions the water either disappears from sight or is evenly dispersed throughout the MCF. With time, if it doesn't all react, it will float to the top of the MCF. The purity of good MCF can drop by 1% in less than a week due to contact with a slight amount of water. Pure distilled water has been used to quickly wash MCF and then the pH of the wash water noted immediately. The pH was always 1 or less for each successive wash of the 99% pure MCF, using fresh water each time.

Phosgene should be no problem in that the "flash-off" should quickly and easily remove it. The problem is the reuse or destruction of the exiting phosgene gas from the reaction loop, and distillation. This can be solved quite simply by scrubbing all the HCl, methyl chloride, and phosgene out with a mix of water, methyl alcohol, and caustic, but this is expensive.

Those skilled in the art need not be reminded that both raw materials and products in processes of this sort are both toxic and corrosive, and that very substantial care is required in both construction and operation thereof.

OBJECTS OF THE INVENTION

A general object of the present invention is to provide an improved method of producing methyl chloroformate.

Another object of the present invention is to provide a method of producing methyl chloroformate of +95% purity, wherein impurities are conveniently and inexpensively removed, because there are fewer of them.

A still further object of the present invention is to provide a method of producing methyl chloroformate wherein production of water and methyl chloride are minimized.

Yet another object of the present invention is to provide a process for producing methyl chloroformate that is adapted for continuous and, with appropriate precautions, safe operation.

Various other objects and advantages will become apparent from the following detailed description of an embodiment thereof, and the novel features will be particularly pointed out in connection with the appended claims.

THE DRAWING

Reference will hereinafter be made to the accompanying drawing, which is a simplified, schematic flow sheet or flow diagram of the equipments utilized in carrying out an embodiment of the invention.

DESCRIPTION OF EMBODIMENTS

Understanding of the invention will be facilitated by considering the equipment illustrated in the drawing, and reference is made thereto.

A phosgene generator 10 has inputs for chlorine 12 and carbon monoxide 14, and is packed with an activated carbon catalyst. The phosgene generator is entirely conventional and per se forms no part of the invention; purchased phosgene of CP grade could be used. The phosgene should preferably be cooled to under 20° C. in heat exchanger 16, unless it is already at this temperature. Fresh methanol in line 18 is added to the circulating MCF product in a static mixer 20, and is cooled to 11° C. in a heat exchanger 22. It is very important that the liquid methanol be rapidly dispersed in the circulating MCF. Were it not, local "hot spots" caused by the reaction of methanol and phosgene could occur, with consequent side reactions, drops in yield, etc. To this end, static mixer 20 is preferred. Having no moving parts, there is no energy input that would tend to raise temperatures. For the same reasons, the optimum point for the methanol injection is just ahead of heat exchanger 22. Temperatures throughout the plant are moderated by use of circulating MCF in a ratio of about 50 to 1 in relation to production rate. Thus, in line 24 the concentration of free methanol is only 1–2%. The phosgene is absorbed in the circulating load by counter-current contact in a tower 26, which is packed with glass Rashig rings or other non-catalytic packing that is also non-porous. Teflon (trademark) is another suitable packing material. This tower is also provided with cooling (not shown) to prevent temperature build-up. It is to be noted that, if exchanger 16 was operated to liquefy the phosgene, tower 26 would be unnecessary.

The circulating load and the reactants pass in line 28 from the bottom of tower 26 into reactor vessel 30, which is cooled by jacket 32. As noted, success of the process requires that the contents of vessel 30 be maintained below 20° C., preferably about 15° C. Vessel 30 is agitated, and sized so that average holding time therein is in the range of 15 to 20 minutes.

Product and the circulating load are drawn off vessel 30 in line 32 by recirculation pump 34. A side stream, in line 36, comprises crude product (about 90%MCF), and amounts to about 1–2% of the circulating load.

The main portion of the circulating load, about 90%, returns to tower 26 in line 24. The remainder is recycled to vessel 30 in line 38, where it helps reduce the cooling load on jacket 32.

The crude product in line 36 is heated to about 71° C. with steam (or hot water) from line 39 in preheater 40, and passes into reboiler tower 42 at an intermediate level. Tower 42 is also packed with glass Rashig rings, and its bottom 44 is also maintained at about 71° C. by steam from line 39.

The feed to tower 42 is about 90% MCF, and the function of tower 42 is to raise this purity to about 98% while reducing yield of MCF as little as possible. To this end, a small stream 46 of light heads is condensed at the top of the tower in condenser 48, run at about 20° C. While condensate in line 46 runs about 85% MCF, its volume is small, and it contains substantially all of the unreacted methanol and most water. Overhead from condenser 48, comprising major proportions of phosgene and HCl, and minor proportions of MCF, $CO_2$ and methyl chloride, are returned to tower 26 via line 50.

Pure product from bottom 44 of tower 42 is passed in line 52 through exchanger 54 and to MCF storage. Exchanger 54 cools the product back to 20° C. or less for storage. Line 52 may be vented via 56 back to line 50 of passage of any non-condensibles.

Gaseous offtake the process is overhead from tower 26, in line 58. A condenser 60 cools the stream to about 3° C., and any condensate is returned to reactor 30 via lines 62 and 59. Non-condensible overhead gas is preferably sent through an HCl adsorbtion tower and the remaining gases are scrubbed.

The initial MCF charge is about three times the maximum amount of MCF produced per hour. So, at the end of one hour, the mole ratio is about 1:3 of produced MCF vs. starting MCF. At the end of three hours the ratio, although all the MCF is not in the loop reactor because of size, is 1:1. Flow rates are much higher, as previously indicated.

Since phosgene should always be in excess of methanol, it is preferred that a certain amount of phosgene be initially dissolved in the initial charge of MCF; about 10 wt.-% excess phosgene is satisfactory.

The carbon monoxide, chlorine, and methanol flow rates are set, based on methanol, in accordance with stoichiometry and desired excess. Methanol is taken as the base with regard to stoichiometric calculations since carbon monoxide, chlorine, and hence phosgene should be in excess to it to avoid DMC and low purity MCF. Phosgene is preferably run in at about 5 mole-% excess to the methanol. This excess phosgene, along with the starting excess of phosgene already dissolved in the MCF, insures an excess of phosgene throughout the reaction. This is true even though some phosgene is taken off in the MCF, which is pumped over and purified. Yet, there is never a dangerous excess of phosgene, because of general losses throughout the reaction along with MCF and HCl gas. This loss cannot be calculated, but is not great, or methanol would be in excess, and lower purity MCF would be obtained. There is also some loss of phosgene when the low boiling impurities (HCl, phosgene, and methanol) are "flashed off" in the still. Proper operation leaves about a 10 wt.-% phosgene-rich MCF solution in the loop reactor at all times. This is confirmed by the usually low excess methanol flashed off by the still and the low DMC content.

The temperature of the reaction, MCF flow rate around the loop, flow rates of especially the chlorine and carbon monoxide, and the exit temperature of the phosgene reactor cooling water are all tightly linked to each other. The importance of maintaining the reaction temperature below 20° C., and preferably at about 15° C. or in the range of 11°–16° C., and of avoiding catalytic packing materials, must be emphasized.

Phosgene is soluble in the range of 48 wt.-% at 0° C. in MCF to 2.5 wt.-% or less at 16° C. Because of this solubility of phosgene, the MCF reaction is run at 15° C. Higher temperatures drive off most of the phosgene before it has a chance to react with the liquid methyl alcohol. Lower temperatures tend to slow the reaction rate down. At 15° C. roughly 15 wt.-% phosgene is soluble in MCF. Also, above 15° C., MCF is more easily evaporated, so greater losses in yield can occur. Condenser 60 should be capable of 0° C. or lower temperatures, to drop back any escaping phosgene gas or MCF vapor in the HCl exit gas, via line 59, to tower 26.

EXAMPLES

Set forth below in Tables I and II are operating data and results for 13 runs employing the process of the invention. In Table II, "GC" refers to gas chromatography, "Finish" refers to high grade product, and "Distillate" refers to light heads in line 46. It will be seen that, after Run 1, product purity was consistently in the range of 95–99%. Further, it is apparent that if one starts with 99% MCF in reactor 32, it is possible to maintain such purity in the net product. Table III reports analyses, temperatures and relative flow rates based on methanol, in ten separate lines of the plant.

Data in Tables I–III are considered to be illustrative only, and are not to be interpreted in a limiting sense.

TABLE I:
OPERATING DATA

| Run | °C. Room Temp. | Avg. °C. Temperature Chiller | Pot | Mid Loop | Cl Flow g-m/hr. | CO Flow g-m/hr. | MeOH Flow g-m/hr. | Yield 100% Pure MCF g-m/hr. | Excess Phosgene g-m/hr. | (1) Excess Phosgene mole-% | Max. Excess Phosgene wt-%(2) |
|---|---|---|---|---|---|---|---|---|---|---|---|
| 1 | 31 | 8.75 | 15.34 | 16.63 | 68.00 | 36.73 | 31.71 | 19.76 | 2.29 | 7.22 | 12.13 |
| 2 | 25 | — | 15.53 | 18.49 | 69.70 | 38.40 | 35.68 | *23.09 | −0.83 | −2.33 | −10.56 |
| 3 | 29.5 | — | 15.16 | 15.02 | 66.81 | 40.20 | 24.21 | 21.70 | 9.20 | 37.98 | 44.37 |
| 4 | 26 | — | 14.13 | 15.31 | 59.34 | 35.27 | 31.48 | *22.93 | −1.81 | −5.75 | −8.26 |
| 5 | 26 | 6.75 | 15.14 | 16.02 | 61.02 | 35.93 | 30.11 | 23.12 | 0.40 | 1.33 | 1.81 |
| 6 | 27 | 5.98 | 12.32 | 13.66 | 65.81 | 39.17 | 29.82 | 24.78 | 3.09 | 10.35 | 13.05 |
| 7 | 27.5 | 2.13 | 11.23 | 12.27 | 62.97 | 37.25 | 32.84 | *24.95 | −1.36 | −4.13 | −5.70 |
| 8 | 28 | 6.86 | 13.73 | 14.77 | 65.09 | 41.70 | 27.28 | 23.02 | 5.27 | 19.30 | 23.96 |
| 9 | 21.5 | 4.43 | 13.29 | 15.32 | 62.89 | 39.58 | 28.68 | 22.66 | 2.77 | 9.64 | 12.79 |
| 10 | 24 | 2.69 | 13.47 | 14.45 | 65.82 | 37.56 | 28.14 | 21.43 | 4.77 | 16.95 | 23.29 |
| 11 | 22.5 | 5.93 | 13.55 | 14.67 | 60.65 | 36.22 | 27.83 | 22.46 | 2.50 | 8.97 | 11.65 |
| 12 | 24 | 6.75 | 13.45 | 14.55 | 67.09 | 41.91 | 25.66 | 20.91 | 7.89 | 30.73 | 39.49 |
| 13 | 22 | 4.32 | 14.94 | 15.54 | 78.90 | 41.16 | 28.44 | 20.90 | 11.01 | 38.71 | 55.13 |

*MCF Yield Based on Chlorine
(1) Based on MeOH
(2) Based on 100% pure MCF Recovered

TABLE II:
OPERATING RESULTS

| Run | G.C. Finish % MeOH | % MCF | % DMC | % Unk. | % MeOH | % MCF | G.C. Distillate % DMC | % Unk. | % Yield |
|---|---|---|---|---|---|---|---|---|---|
| 1 | 1.50 | 93.26 | 5.24 | — | 4.54 | 87.98 | 2.04 | 5.44 | 62.32 |
| 2 | 0.73 | 95.80 | 2.74 | 0.73 | 6.83 | 91.03 | 2.14 | — | 66.26 |
| 3 | 1.30 | 94.30 | 2.93 | 1.47 | 14.08 | 84.56 | 1.36 | — | 89.63 |
| 4 | — | 96.24 | 2.66 | 1.25[2] | 0.22 | 89.05 | 9.48 | 1.10 | 77.28 |
| 5 | — | 94.97 | 3.28 | 1.75 | 1.39 | 93.05 | 2.67 | 2.89[2] | 76.79 |
| 6 | 0.72 | 93.55 | 3.58 | 2.15 | 2.72 | 94.05 | 1.53 | 1.70 | 83.10 |
| 7 | — | 95.27 | 4.73 | — | 2.98 | 97.02 | — | — | 79.24 |
| 8 | — | 95.12 | 4.88 | — | 7.08 | 92.92 | — | — | 84.38 |
| 9 | 0.81 | ᵃ96.95 | 2.24 | — | 2.49 | 96.14 | — | 1.37 | 79.01 |
|  |  | ᵇ97.45 | 2.55 | — |  |  |  |  |  |
| 10 | — | ᵃ97.89 | 2.11 | — | 1.55 | 96.63 | — | 1.81 | 76.15 |
|  | — | ᵇ98.24 | 1.76 | — |  |  |  |  |  |
| 11 | 0.89 | ᵃ99.11 | — | — | 4.85 | 95.15 | — | — | 80.70 |
|  | 1.53 | ᵇ98.47 | — | — |  |  |  |  |  |
| 12 | 0.83 | ᵃ97.52 | 1.65 | — | 12.74 | 86.16 | 1.10 | — | 81.49 |
|  | 1.54 | ᵇ98.46 | — | — |  |  |  |  |  |
| 13 | 1.01 | ᵃ95.48 | 2.35 | 1.16 | 12.30 | 85.41 | — | 2.29 | 73.49 |
|  | 0.96 | ᵇ96.34 | 1.74 | 0.96 |  |  |  |  |  |

ᵃPurity of first ⅓ run
ᵇPurity of last ⅓ run
[2]Two unknowns

TABLE III

| Line | 15 | 18 | 52 | 46 | 32 | 36 | 38 | 24 | 50 |
|---|---|---|---|---|---|---|---|---|---|
| FLOW NAME | COCL$_2$ | MeOH | 98% MCF | LIGHT HEADS | MCF | MCF | MCF | MCF | COCL$_2$ |
| FLOW RATIO | 3.3 | 1.0 | 2.7 | 0.14 | 263.1 | 3.3 | 37.0 | 222.7 | 0.47 |
| PROD. CON. % | 96.4 | 99.5 | 98.0 | 85.5 | 89.4 | 89.4 | 88.9 | 88.9 | 41.3 |
| °C | 70 | 20 | 30 | 20 | 15 | 15 | 11 | 11 | 20 |
| CONCENTRATION OF COMPONENTS |  |  |  |  |  |  |  |  |  |
| MCF% | — | — | 98.0 | 85.5 | 89.4 | 89.4 | 88.9 | 88.9 | 15.9 |
| MeOH% | — | 99.5 | 0.4 | 10.5 | 1.1 | 1.1 | 1.6 | 1.6 | 0.7 |
| COCL$_2$% | 96.4 | — | — | — | 5.9 | 5.9 | 5.9 | 5.9 | 41.3 |
| HCL% | — | — | 0.2 | 0.2 | 3.2 | 3.2 | 3.2 | 3.2 | 23.0 |
| MeCL% | — | — | 0.6 | 0.0 | 0.2 | 0.2 | 0.2 | 0.2 | 9.2 |
| CO% | 3.6 | — | — | — | — | — | — | — | — |
| CO% | — | — | — | — | — | — | — | — | 9.8 |
| Line | 15 | 18 | 52 | 46 | 30 | 36 | 38 | 24 | 30 |
| H$_2$O% | — | — | — | 3.8 | 0.2 | 0.2 | 0.2 | 0.2 | 0.1 |
| DMC% | — | — | 0.8 | — | — | — | — | — | — |

Various changes in the details, steps, materials and arrangements of parts, which have been herein described and illustrted to explain the nature of the invention, may be made by those skilled in the art within the principle and scope of the invention as defined in the appended claims.

What is claimed is:

1. In the process for the production of methyl chloroformate by reaction of phosgene and methyl alcohol, the improvements comprising:

carrying out said reaction in the liquid phase in the presence of a large circulating load of preformed methyl chloroformate, in the absence of catalytic materials and at a temperature constantly under 20° C.;

absorbing said phosgene in said preformed methyl chloroformate;

rapidly dispersing said methanol in a flowing stream of said preformed methyl chloroformate;

said circulating load and heat exchangers preventing undesired temperature rises.

2. The process as claimed in claim 1, wherein said preformed methyl chloroformate comprises at least 97% of the reaction mixture.

3. The process as claimed in claim 1 wherein:

phosgene gas is absorbed in said methyl chloroformate;

said reaction is carried out at about 15° C.; and a portion of methyl chloroformate is withdrawn as product.

4. The process as claimed in claim 1 wherein:

liquid phosgene is rapidly dispersed in said preformed methyl chloroformate;

said reaction is carried out at about 15° C.; and a portion of methyl chloroformate is withdrawn as product.

5. The process as claimed in claim 3, and additionally comprising heating said product stream to no more than about 71° C. at atmospheric pressure to remove substantially all impurities but only a minor proportion of said product.

6. The process as claimed in claim 3, wherein said phosgene is absorbed in a packed column, said packing being non-porous and non-catalytic.

7. The process for producing methyl chloroformate comprising:

rapidly dispersing methyl alcohol into a flowing stream of methyl chloroformate in a volume ratio of about 1 - 50;

absorbing phosgene gas in said methyl chloroformate;

constantly maintaining the reaction mixture in the range of 11° to 16° C., with the formation of additional chloroformate;

withdrawing a minor proportion of said reaction mixture as product; and recycling the major portion of said mixture to said dispersing step.

8. The process as claimed in claim 7, wherein at least 97% of said reaction mixture is methyl chloroformate.

9. The process as claimed in claim 7 and additionally comprising heating said product to no more than about 71° C. at atmospheric pressure, thereby removing substantially all impurities as vapors but only a minor proportion of said product.

10. The process as claimed in claim 7, wherein in said absorption step is carried out in a packed column, said packing being non-porous and non-catalytic.

11. A continuous process for the production of high purity methyl chloroformate comprising:

maintaining a large volume of methyl chloroformate in the range of 11° to 16° C. and circulating between a reactor and an absorber;

rapidly dispersing methyl alcohol in a circulating stream of said methyl chloroformate;

continuously absorbing phosgene gas in said methyl chloroformate in said absorber;

said phosgene and methyl alcohol comprising no more than about 2 % of the reaction mixture at any time;

continuously withdrawing a small portion of the reaction mixture from said reactor as product; and heating said product to no more than about 71° C at atmospheric pressure thereby removing substantially all impurities as vapors but only a minor proportion of product.

12. The process as claimed in claim 11, wherein dispersion of said methyl alcohol is carried out in a static mixer, and additionally comprising immediately cooling said stream following dispersion, thereby avoiding localized temperatures higher than 20° C.

13. The process as claimed in claim 11, wherein said absorber contains a non-porous, non-catalytic packing.

14. The process as claimed in claim 11, wherein said large volume of methyl chloroformate has phosgene dissolved therein.

15. The process as claimed in claim 11, wherein the average holding time of the reaction mixture in said reactor is in the range of 15 to 20 minutes.

* * * * *